United States Patent [19]

Watanabe et al.

[11] 4,170,530

[45] Oct. 9, 1979

[54] OXYGEN CONCENTRATION CELL AND A METHOD OF PRODUCING THE SAME

[75] Inventors: Tetsuo Watanabe, Nagoya; Shigetaka Wada, Kuwana, both of Japan

[73] Assignee: NGK Insulators, Ltd., Nagoya, Japan

[21] Appl. No.: 875,566

[22] Filed: Feb. 6, 1978

[30] Foreign Application Priority Data

Feb. 16, 1977 [JP] Japan .................................. 52-14915

[51] Int. Cl.² .............................. G01N 27/46; 427/126
[52] U.S. Cl. .................................. 204/195 S; 204/1 T
[58] Field of Search .............................. 204/15, 195 S; 429/33; 427/126

[56] References Cited

U.S. PATENT DOCUMENTS

| | | | |
|---|---|---|---|
| 3,300,344 | 1/1967 | Bray et al. | 429/33 |
| 3,843,400 | 10/1974 | Radford et al. | 204/195 S |
| 3,978,006 | 8/1976 | Topp et al. | 204/195 S |
| 4,040,929 | 8/1977 | Bauer et al. | 204/195 S |
| 4,080,276 | 3/1978 | Bode | 204/195 S |

OTHER PUBLICATIONS

SAE Paper 750,223, "Ceramic Aspects of the Bosch Lamda-Sensor", 1975, pp. 1-18.

*Primary Examiner*—T. Tung
*Attorney, Agent, or Firm*—Stevens, Davis, Miller & Mosher

[57] ABSTRACT

An oxygen concentration cell capable of operating at a lower temperature and having a higher response speed is disclosed. The cell consists of an oxygen ion conductive solid electrolyte provided on both of its surfaces with electrodes consisting of a porous electrically conductive layer, which is formed of a platinum group metal and contains in its pores a metal oxide formed by the thermal decomposition of an oxide-forming metal compound.

4 Claims, No Drawings

OXYGEN CONCENTRATION CELL AND A METHOD OF PRODUCING THE SAME

BACKGROUND OF THE INVENTION

1. Field of the Invention

The present invention relates to an oxygen concentration cell, which operates even at a lower temperature and has a more rapid response speed, and a method of producing the same.

2. Description of the Prior Art

It has been known that a sintered article of zirconium oxide stabilized with CaO, $Y_2O_3$ or the like is an oxygen ion conductive solid electrolyte having an oxygen ion transport number of about 1.0, and that an element consisting of the oxygen ion conductive solid electrolyte provided on its surfaces with porous platinum electrodes or the like serves as an oxygen concentration cell, which is used as a sensor for measuring the oxygen partial pressure in the waste gas of a boiler or in the exhaust gas of an internal combustion engine, or is used as a fuel cell.

When an oxygen concentration cell is used as an oxygen sensor, the cell is required to generate an electromotive force at a lower temperature and to have a more rapid response speed relative to the variation of oxygen partial pressure. Particularly, when the cell is used as a sensor for measuring the oxygen partial pressure in the exhaust gas of an internal combustion engine, the cell is required to have electrodes tightly adhered to the cell, because the cell is exposed to thermal shock and high speed exhaust gas.

A simplified electric equivalent circuit of an oxygen concentration cell can be expressed by a series circuit consisting of the interfacial impedance between electrodes and solid electrolyte, the impedance of solid electrolyte itself and the electromotive force. The impedance of solid electrolyte itself depends substantially upon its composition when the electrolyte is sufficiently densely sintered, and the electromotive force is determined by the well-known Nernst equation. However, it is known that the interfacial impedance is highly influenced by the kind of materials for the porous electrode and the applying method of the electrode. Therefore, in order to obtain an oxygen concentration cell capable of generating an electromotive force at a lower temperature and having a more rapid response speed, it is necessary to provide porous electrodes having a proper amount of pores and capable of giving a low interfacial impedance.

Platinum group metals are generally used as the electrode of oxygen concentration cells of this kind, and as the method of applying an electrode formed of platinum group metal, there have been known chemical plating methods, physical plating methods, baking methods and the like. As the oxygen concentration cell is provided with electrodes capable of generating an electromotive force at a lower temperature, that is, electrodes having a low interfacial impedance, there has been known an oxygen concentration cell provided with cermet-like electrodes consisting of a sintered mixture obtained by applying a mixture consisting of powders or finely divided particles of a platinum group metal and powders or finely divided particles of an oxygen ion conductive solid electrolyte to an oxygen ion conductive solid electrolyte substrate, and baking the mixture to the solid electrolyte substrate. However, the cermet-like electrode of this oxygen concentration cell is generally baked at a temperature of about 1,300–1,400° C. in order to generate an electromotive force at a lower temperature and to obtain a higher response speed. However, when a baking is effected at such temperature, the solid electrolyte powder in the mixture is not integrally sintered with the solid electrolyte substrate, and the resulting electrode is poor in the mechanical strength and is easily exfoliated by mechanical friction. While, when a baking is carried out at a temperature of not lower than 1,4000° C. in order to obtain an electrode having a higher resistance against mechanical friction and a higher adhesion strength, the resulting cell generates an electromotive force at a lower temperature, but is low in the response speed. Accordingly, the development of an oxygen concentration cell capable of generating an electromotive force at a lower temperature and having a higher response speed has been eagerly demanded.

SUMMARY OF THE INVENTION

The object of the present invention is to provide an oxygen concentration cell which can eliminate the above mentioned drawbacks.

The feature of the present invention is the provision of an oxygen concentration cell consisting of an oxygen ion conductive solid electrolyte provided on both of its surfaces with electrodes, each electrode consisting of a porous electrically conductive layer, which consists of a platinum group metal and contains in its pores a metal oxide, preferably zirconium oxide, formed by the thermal decomposition of an oxide-forming metal compound.

DETAILED DESCRIPTION OF THE INVENTION

As the oxygen ion conductive solid electrolyte, use is made of zirconium oxide and the like stabilized with yttrium oxide, calcium oxide and the like. As the metal oxide, use is made of zirconium oxide, aluminum oxide, yttrium oxide, thorium oxide, hafnium oxide and the like.

The electrode consisting of a porous electrically conductive layer, which consists of a platinum group metal and contains in its pores a metal oxide formed by the thermal decomposition of an oxide-forming metal compound can be produced in the following manner. A solution of an oxide-forming metal compound, preferably an aqueous solution of zirconium oxychloride, is applied to a porous electrically conductive layer consisting of a platinum group metal, and the oxide-forming metal compound is converted into a metal oxide by a thermal decomposition directly or after the solution is exposed to ammonia gas to deposit from the solution a compound, for example, zirconium hydroxide, insoluble or hardly soluble in the solvent of the solution and to prevent the flow down of the solution of the metal compound. The electrode having a desired thickness can be obtained by repeating the above described procedure several times.

The electrode can also be produced by the following methods. A mixture of finely divided particles of a platinum group metal with a solution of an oxide-forming metal compound is applied to a solid electrolyte, and the metal compound is thermally decomposed. Alternatively, a solution of a mixture of a compound of platinum group metal and an oxide-forming metal compound is applied to a solid electrolyte, and the metal compound is thermally decomposed. As the solution of oxide-forming metal compound, use may be made of solutions, preferably aqueous solutions, of chlorate, sulfate, chloride, nitrate and the like of metal.

Of course, even if the metal oxide formed by the thermal decomposition of a solution of oxide-forming metal compound would be adhered to the surface of the porous electrically conductive layer, the metal oxide is not affected adversely.

The reason why an oxygen concentration cell provided with electrodes consisting of a porous electrically conductive layer, which consists of a platinum group metal and contains in its pores a metal oxide, has a lower internal resistance and a more rapid response speed is probably that the metal oxide formed by the thermal decomposition of the oxide-forming metal compound is contained in the pores of the porous platinum group metal layer such that gaps having proper dimensions remain therein and that a large number of contact points are uniformly formed between the platinum group metal and the solid electrolyte.

Moreover, even when the cell is exposed to a high temperature and the platinum group metal constituting the electrode is sintered, neither excessively large pores are formed, nor are the number of contact points between the platinum group metal and the solid electrolyte decreased, nor are the surface area of the platinum group metal decreased. Therefore, the durability of the cell is excellent at high temperature and the decrease of the activity of the cell is very small even at high temperature.

The following examples are given for the purpose of illustration of this invention and are not intended as limitations thereof.

EXAMPLE 1

A powdery mixture consisting of 90 mol% of zirconium oxide and 10 mol% of yttrium oxide was pressed and fired at 1,750° C. to produce a solid electrolyte disk having a diameter of 25 mm and a thickness of 1 mm and having a density of 5.65 g/cm$^3$. An aqueous solution of platinum tetrachloride was applied to the central portion of both surfaces of the solid electrolyte disk in an area of 20 mm diameter, and the solution was baked at 1,000° C. thereto to form porous electrically conductive layers consisting of platinum on both surfaces of the disk.

Then, an aqueous solution of zirconium oxychloride was applied to the porous electrically conductive platinum layers and fired at 1,000° C. to form electrodes on both surfaces of the solid electrolyte disk, each electrode consisting of a porous electrically conductive platinum layer containing in its pores zirconium oxide formed by the thermal decomposition of the zirconium oxychloride, whereby an oxygen concentration cell of the present invention (cell No. 1) was obtained.

The internal resistance of the resulting oxygen concentration cell inclusive of its interfacial impedance was measured at 500° C. in air. Further, the oxygen concentration cell was heated while contacting one of the electrode surfaces of the cell with air and another electrode surface with nitrogen gas containing 5% of hydrogen, and a temperature, at which an electromotive force of 0.7 volt was induced, was measured.

Further, the oxygen concentration cell was kept at 500° C., and one of the electrode surfaces of the cell was contacted with air, and another electrode surface was firstly contacted with nitrogen gas containing 5% of hydrogen and then contacted with air, and a response time required for decreasing the electromotive force of the cell from about 1.0 volt to 0.2 volt was measured. The above obtained results are shown in the following Table 1.

Table 1

| Cell No. | Method of forming electrodes | | Temperature at which an electromotive force of 0.7 volt is induced (° C.) | Internal resistance at 500° C. (KΩ) | Response time (sec.) | Remarks |
| --- | --- | --- | --- | --- | --- | --- |
| | Platinum | Metal oxide | | | | |
| Cell of the present invention | | | | | | |
| 1 | Aqueous solution of platinum tetrachloride is applied and baked at 1,000° C. | Aqueous solution of zirconium oxychloride is applied and thermally decomposed at 1,000° C. | 240 | 0.4 | 1.6 | |
| 2 | Aqueous solution of platinum tetrachloride is applied and baked at 1,000° C. | Aqueous solution of aluminum chloride is applied and thermally decomposed at 1,000° C. | 290 | 0.7 | 2.1 | Electrode layer is very strongly adhered to solid electrolyte disk |
| 3 | Aqueous solution of platinum tetrachloride is applied and baked at 1,000° C. | Aqueous solution of zirconium sulfate is applied and thermally decomposed at 1,000° C. | 260 | 0.5 | 1.9 | |
| 4 | Paste of finely divided platinum powders is baked at 1,100° C. | Aqueous solution of zirconium oxynitrate is applied and thermally decomposed at 1,000° C. | 250 | 0.5 | 1.8 | |
| 5 | The same procedures as those in cell No. 1 are alternately repeated 3 times | | 240 | 0.4 | 1.8 | |
| Comp. cell | | | | | | |
| 6 | Aqueous solution of platinum tetrachloride is applied and baked at 1,000° C. | — | 350 | 9.3 | 5.8 | Electrode layer is very strongly adhered to solid electrolyte disk |
| 7 | Paste of a mixture of finely divided platinum powders | | 310 | 1.9 | 3.2 | Electrode layer is easily exfoliated from |

Table 1-continued

| Cell No. | Method of forming electrodes — Platinum | Method of forming electrodes — Metal oxide | Temperature at which an electro-motive force of 0.7 volt is induced (° C.) | Internal resistance at 500° C. (KΩ) | Response time (sec.) | Remarks |
|---|---|---|---|---|---|---|
| | | and finely divided powders of stabilized zirconia is baked at 1,300° C. | | | | solid electrolyte disk by friction |
| 8 | | The same paste as used in cell No. 7 is baked at 1,500° C. | 330 | 3.8 | 10.5 | Electrode layer is relatively strongly adhered to solid electrolyte disk |
| 9 | Same as in cell No. 1 | (Hydrochloric acid is applied) | 360 | 11.1 | 5.5 | Electrode layer is very strongly adhered to solid electrolyte |
| 10 | Same as in cell No. 4 | — | 380 | 16.7 | 6.4 | disk |

EXAMPLE 2

An aqueous solution of platinum tetrachloride was applied to the central portion in an area of 20 mm diameter of both surfaces of a solid electrolyte disk produced in the same manner as described in Example 1, and baked thereto at 1,000° C. to form porous electrically conductive layers consisting of platinum on both surfaces of the disk.

Then, an aqueous solution of aluminum chloride was applied to the porous electrically conductive platinum layer and fired at 1,000° C. to form electrodes on both surfaces of the disk, each electrode consisting of a porous electrically conductive platinum layer containing in its pores aluminum oxide formed by the thermal decomposition of the aluminum chloride, whereby an oxygen concentration cell of the present invention (cell No. 2) was obtained.

With respect to the resulting cell, the internal resistance at 500° C. in air, the temperature at which an electromotive force of 0.7 volt was induced, and the response time at 500° C. were measured in the same manner as described in Example 1. The obtained results are shown in Table 1.

EXAMPLE 3

An aqueous solution of platinum tetrachloride was applied to the central portion in an area of 20 mm diameter of both surfaces of a solid electrolyte disk produced in the same manner as described in Example 1, and baked thereto at 1,000° C. to form porous electrically conductive layers consisting of platinum on both surfaces of the disk.

Then, an aqueous solution of zirconium sulfate was applied to the porous electrically conductive platinum layer and fired at 1,000° C. to form electrodes on both surfaces of the disk, each electrode consisting of the porous electrically conductive platinum layer containing zirconium oxide formed by the thermal decomposition of the zirconium sulfate, whereby an oxygen concentration cell of the present invention (cell No. 3) was obtained.

With respect to the resulting cell, the internal resistance at 500° C. in air, the temperature at which an electromotive force of 0.7 volt was induced, and the response time at 500° C. were measured in the same manner as described in Example 1. The obtained results are shown in Table 1.

EXAMPLE 4

A paste of finely divided particles of platinum added to water was applied to the central portion in an area of 20 mm diameter on both surfaces of a solid electrolyte disk produced in the same manner as described in Example 1, and baked thereto at 1,100° C. to form porous electrically conductive layers consisting of platinum on both surfaces of the disk.

Then, an aqueous solution of zirconium oxynitrate was applied to the porous electrically conductive platinum layer and fired at 1,000° C. to form electrodes on both surfaces of the disk, each electrode consisting of the porous electrically conductive platinum layer containing in its pores zirconium oxide formed by the thermal decomposition of the zirconium oxynitrate, whereby an oxygen concentration cell of the present invention (cell No. 4) was obtained.

The internal resistance of the resulting cell at 500° C. in air, the temperature at which an electromotive force of 0.7 volt is induced in the cell, and the response time at 500° C. of the cell are shown in Table 1.

EXAMPLE 5

An aqueous solution of platinum tetrachloride was applied to the central portion in an area of 20 mm diameter on both surfaces of a solid electrolyte disk produced in the same manner as described in Example 1 and baked thereto at 1,000° C. to form porous electrically conductive layers consisting of platinum on both surfaces of the disk. Then, an aqueous solution of zirconium oxychloride was applied to the porous electrically conductive platinum layers and exposed to ammonia gas to convert the zirconium oxychloride to water-insoluble zirconium hydroxide, and then fired at 1,000° C. The above described procedures: application of aqueous solution of platinum tetrachloride to the disk—formation of porous electrically conductive platinum layer on the disk by baking—application of an aqueous solution of zirconium oxychloride to the porous layer—exposure of the zirconium oxychloride solution to ammonia gas to convert the zirconium oxychloride into water-insoluble zirconium hydroxide—firing: were repeatedly carried out 3 times to form electrodes on both surfaces of the disk, each electrode consisting of a porous electrically conductive platinum layer containing in its pores zirconium oxide formed by the thermal decomposition of the zirconium oxychloride, whereby an oxygen concentration cell of the present invention (cell No. 5) was obtained.

The internal resistance of the resulting cell at 500° C. in air, the temperature at which an electromotive force of 0.7 volt was induced in the cell, and the response time of the cell at 500° C. are shown in Table 1.

For comparison, comparative oxygen concentration cells of Nos. 6, 7, 8, 9 and 10 were produced in the following manner by the use of the same solid electrolyte disk as used in Example 1. In the production of cell No. 6, porous platinum electrodes containing no metal oxide in its pores were formed on both surfaces of the disk. In the production of cell No. 7 or 8, cermet electrodes were formed by baking a paste of a mixture of finely divided platinum particles and finely divided particles of zirconium oxide stabilized with yttrium in water, at 1,300° C. or 1,500° C. respectively to both surfaces of the disk. Further, since the solution of metal compound for obtaining metal oxide is strongly acidic, cell Nos. 9 and 10 were produced in order to examine the influence of acid. In the production of cell No. 9, only an acid solution was applied to porous electrodes consisting of platinum and the above treated electrodes were heat-treated. In the production of cell No. 10, porous electrically conductive layers were formed by the use of a paste of finely divided platinum particles in water, but procedures of the application of an oxide-forming metal compound solution and the thermal decomposition of the metal compound were not effected. With respect to these comparative cells, the internal resistance at 500° C. in air, the temperature at which an electromotive force of 0.7 volt was induced, and the response time at 500° C. were measured, and the obtained results are shown in Table 1.

It can be seen from Table 1 that the oxygen concentration cell of the present invention has a lower internal resistance, generates electromotive force at a lower temperature and is short in the response time. On the contrary, the oxygen concentration cell provided with porous platinum electrodes containing no metal oxide in its pores has a higher internal resistance and is short in the response time. The oxygen concentration cell provided with cermet electrodes is poor in the strength of the electrodes themselves and is long in the response time even though the cell generates electromotive force at a low temperature. That is, the comparative cells are inferior to the cell of the present invention.

As described above, the oxygen concentration cell of the present invention is provided with electrodes consisting of a porous layer, which consists of a very fine network formed of a platinum group metal and contains in its pores a metal oxide formed by the thermal decomposition of an oxide-forming metal compound so as to form gaps having proper dimensions in the pores and to form uniformly a large number of contact points between the platinum group metal and the solid electrolyte. Therefore, the oxygen concentration cell of the present invention can generate electromotive force at a lower temperature, and is short in the response time and excellent in the high-temperature resistance. Therefore, the decrease of the activity of the cell is very small even at high temperature, and the cell is particularly useful as an oxygen sensor for measuring the oxygen partial pressure in the exhaust gas of internal combustion engines.

What is claimed is:

1. An oxygen concentration cell consisting of an oxygen ion conductive solid electrolyte provided on its both surfaces with electrodes, each electrode consisting of a porous electrically conductive layer, which consists of a platinum group metal and contains in its pores a metal oxide formed in liter by the thermal decomposition of an oxide-forming metal compound.

2. An oxygen concentration cell according to claim 1, wherein said metal oxide is zirconium oxide.

3. A method of producing the oxygen concentration cell according to claim 1, comprising forming porous layers consisting of a platinum group metal on both surfaces of an oxygen ion conductive solid electrolyte, applying a solution of an oxide-forming metal compound to the layers, and converting the metal compound in the solution into a metal oxide by thermal decomposition.

4. A method according to claim 3, wherein said solution of oxide-forming metal compound is an aqueous solution of zirconium oxychloride.

* * * * *